(12) United States Patent
Harel et al.

(10) Patent No.: US 8,034,788 B2
(45) Date of Patent: Oct. 11, 2011

(54) COMPOSITION AND METHODS FOR SKIN CARE

(75) Inventors: Avikam Harel, Tel Aviv (IL); Zeev Even-Chen, Rehovot (IL); Olga Bloch, Petach Tikva (IL)

(73) Assignee: Dermipsor Ltd., Katzrin (IL)

( * ) Notice: Subject to any disclaimer, the term of this patent is extended or adjusted under 35 U.S.C. 154(b) by 620 days.

(21) Appl. No.: 11/914,093

(22) PCT Filed: May 10, 2006

(86) PCT No.: PCT/IL2006/000552
§ 371 (c)(1),
(2), (4) Date: Jun. 10, 2008

(87) PCT Pub. No.: WO2006/120681
PCT Pub. Date: Nov. 16, 2006

(65) Prior Publication Data
US 2008/0312181 A1    Dec. 18, 2008

Related U.S. Application Data

(60) Provisional application No. 60/679,329, filed on May 10, 2005.

(51) Int. Cl.
*A01N 43/04* (2006.01)
*A61K 31/70* (2006.01)

(52) U.S. Cl. ...................................................... 514/23
(58) Field of Classification Search .................. None
See application file for complete search history.

(56) References Cited

U.S. PATENT DOCUMENTS

| | | | | |
|---|---|---|---|---|
| 4,804,502 A | 2/1989 | Baggiolini et al. | ........ | 260/397.2 |
| 4,851,401 A | 7/1989 | DeLuca et al. | ................ | 514/167 |
| 4,866,048 A | 9/1989 | Calverley et al. | ............ | 514/167 |
| 5,120,722 A | 6/1992 | Baggiolini et al. | ........... | 514/167 |
| 5,145,846 A | 9/1992 | Baggiolini et al. | ........... | 514/167 |
| 5,237,110 A | 8/1993 | DeLuca et al. | ................ | 568/665 |
| 5,374,629 A | 12/1994 | Calverley et al. | ............. | 514/167 |
| 5,403,940 A | 4/1995 | Vallés et al. | .................... | 549/300 |
| 5,446,034 A | 8/1995 | Bretting et al. | ............... | 514/167 |
| 5,446,035 A | 8/1995 | Neef et al. | ...................... | 514/167 |
| 5,447,924 A | 9/1995 | Bretting | ........................ | 514/167 |
| 5,747,479 A | 5/1998 | Bryce et al. | .................... | 514/167 |
| 5,804,574 A | 9/1998 | Bryce et al. | .................... | 514/167 |
| 5,811,414 A | 9/1998 | Bryce et al. | .................... | 514/167 |
| 6,262,041 B1 | 7/2001 | Serbinova | ...................... | 514/167 |
| 6,284,234 B1 | 9/2001 | Niemiec et al. | ............. | 424/78.07 |
| 6,288,249 B1 | 9/2001 | Halkes et al. | ................. | 552/653 |
| 6,552,009 B2 | 4/2003 | Achkar | .......................... | 514/168 |
| 6,753,013 B1 | 6/2004 | Didriksen et al. | ............ | 424/484 |
| 6,831,106 B1 | 12/2004 | Bernardon et al. | ........... | 514/730 |

FOREIGN PATENT DOCUMENTS

| WO | WO 01/51051 | | 7/2001 |
|---|---|---|---|
| WO | WO 01/51051 A2 | * | 7/2001 |
| WO | WO 2004/006887 A2 | | 1/2004 |

OTHER PUBLICATIONS

Stuttgen Clinics in Dermatology (1997), vol. 15, pp. 693-703.*
Michel et al. Inflamm. Res. (1997), vol. 46, pp. 32-34.*
International Search Report for PCT/IL06/00552.

* cited by examiner

*Primary Examiner* — Patrick Lewis
(74) *Attorney, Agent, or Firm* — Winston & Strawn LLP

(57) ABSTRACT

Compositions useful in the treatment of skin atrophy and improvement of skin appearance and texture are disclosed. The methods include the topical administration of vitamin D3 or specific vitamin D3 analogs as an essential ingredient either on its own or in combination with cADPR and or nicotinamide. The compositions are particularly effective in preventing and treating signs of chronological and or photo-aging including fine lines, wrinkles and discoloration.

15 Claims, 3 Drawing Sheets

Vitamin D

Vitamin $D_3$

COMPOSITION AND METHODS FOR SKIN CARE

This application claims the benefit of U.S. provisional application 60/679,329 filed May 10, 2005.

FIELD OF THE INVENTION

The present invention relates to compositions useful for effecting an improvement in the appearance and feel of skin. In particular, the present invention provides compositions comprising vitamin $D_3$ or specific analogs thereof as an essential ingredient thereof, and in combination with nicotinamide, cADPR or derivatives thereof, for topical application useful in the prevention and treatment of the signs associated with cutaneous aging and photoaging.

BACKGROUND OF THE INVENTION

Skin and Aging

The skin is the largest organ of the body and functions primarily to protect the body from external factors such as microorganisms, chemicals, UV radiation and temperature. Skin is subject to abuse by environmental, as well as inherent, factors. Environmental factors include exposure to the sun, smoking and air pollution, while inherent factors include stress and chronological aging. Whether extrinsic or intrinsic, the abuse results in visible signs on the skin such as fine lines, wrinkles and discoloration. The prevention, elimination or diminution of these signs has become a multi-billion dollar business with treatments ranging from over-the-counter topical creams and moisturizers to a variety of cosmetic surgery techniques. Normal chronological aging results in the thinning, loss of elasticity and general atrophy of the skin. Chronological aging may be hastened by photoaging, the premature aging of the skin due to exposure to UV radiation (reviewed in Fisher, et al., 2002). Oxidation also contributes to the process of aging by producing unstable molecules, known as free radicals, which are toxic to the skin.

One of the most important issues addressed by the cosmetic industry is that of premature skin aging. Wrinkles can have a profound impact on self-esteem. Indeed, the stigma attached to looking old is evidenced by the fact that in the USA alone, more than $12 billion is spent each year on cosmetics to reverse or conceal the signs of aging.

Vitamin D and the Skin

The term vitamin D refers to the secosterols ergocalciferol (vitamin $D_2$) and cholecalciferol (vitamin $D_3$) as well as to their metabolites and analogs, including alfacalcidol (1hydroxycholecalciferol), calcitriol (1α,25-dihydroxycholecalciferol) and dihydrotachysterol (DHT).

Vitamin D is a prohormone with several active metabolites that act as hormones. In the skin, previtamin $D_3$ is synthesized photochemically from 7-dehydrocholesterol and is slowly isomerized to vitamin $D_3$, which is removed by vitamin D-binding protein. In the liver, vitamin $D_3$ is converted to $25(OH)D_3$, the major circulating form, which passes through the enterohepatic circulation and is reabsorbed from the gut. In the kidneys, it is further hydroxylated to the more metabolically active form, $1α,25(OH)_2D_3$ (1α,25-dihydroxycholecalciferol, calcitriol, vitamin D hormone).

Experimental evidence shows that vitamin D is anti-proliferative and stimulates the terminal differentiation of keratinocytes. In psoriatic lesions, epidermal keratinocytes exhibit hyperproliferation and impaired differentiation triggered by inflammation. Therefore, vitamin D and certain analogs are highly effective in treating psoriasis vulgaris (reviewed in Lehmann et al., 2004). Calcipotriol, a topical antipsoriatic vitamin-$D_3$ derivative is marketed in the United States under the trade name Dovonex®. Calcipotriol is as potent as the naturally occurring calcitriol in regulating cell proliferation, but has the benefit of being much less active in its adverse systemic effect on calcium metabolism.

The art discloses derivatives of vitamin D and vitamin D analogs and compositions comprising the same.

Vitamin D analogs are described in U.S. Pat. No. 4,851,401 (cyclopentano-vitamin D analogs), U.S. Pat. No. 5,120,722 (trihydroxycalciferol derivatives), U.S. Pat. No. 5,446,035 (20-methyl substituted vitamin D), U.S. Pat. No. 5,411,949 (23-oxa-derivatives), U.S. Pat. No. 5,237,110 (19-nor-vitamin D compounds), U.S. Pat. No. 4,857,518 (hydroxylated 24-homo-vitamin D derivatives). Additional Vitamin D analogs are taught in U.S. Pat. Nos. 4,804,502; 4,866,048; 5,145,846 5,374,629; 5,403,940; 5,446,034; and 5,447,924, among others.

U.S. Pat. No. 6,552,009 discloses a composition comprising a vitamin D analog and a derivative of retinoid useful in treating disorders characterized by abnormal cell-proliferation and/or cell-differentiation. In certain preferred embodiments the vitamin D analog is selected from calcitriol and calcipotriol.

U.S. Pat. No. 6,288,249 is directed to novel vitamin D derivatives and to methods for treating osteoporosis and proliferative diseases and to improving skin conditions including dry skin and wrinkles. U.S. Pat. No. 6,831,106 teaches novel vitamin D compounds and pharmaceutical and cosmetic compositions comprising same. The compounds taught in the '249 and '106 patents differ from vitamin D and the classic vitamin D analogs in that they do not comprise the generic 9,10 secosterol structure.

U.S. Pat. No. 6,753,013 describes a pharmaceutical composition for dermal use comprising a combination of a vitamin D analog and a corticosteroid, the composition alleviating the inconvenience of a two-component regimen for the treatment of psoriasis and other inflammatory skin diseases.

U.S. Pat. No. 6,262,041 teaches a method for reducing the rate at which human skin ages or for treating skin cancer, acne or rosacea, the method comprising topically administering 26,27-hexafluoro-1,25-dihydroxy vitamin $D_3$ to the skin on a daily basis in an antioxidative amount for a time sufficient to reduce the rate of skin aging.

U.S. Pat. Nos. 5,747,479; 5,804,574 and 5,811,414 disclose vitamin $D_3$ analogs which are 26,27-hexafluorocholecalciferol derivatives, useful for reversing photodamage in sun-exposed skin. Mitani et al. (Mitani et al., 2004) disclose the topical application of ergocalciferol (vitamin $D_2$) for the suppression of photodamage to the skin.

International Patent Application Publication WO 01/51051 of some of the inventors of the present invention teaches compositions and methods of treating a benign or malignant hyperproliferative epidermal pathology comprising administering to the subject a dermatologically effective amount of an agent selected from the group consisting of nicotinamide and/or cyclic adenosine diphosphate-ribose (cADPR), and analogs thereof.

International Patent Application Publication WO 2004/006887 of some of the inventors of the present invention teaches compositions and methods useful in treating a benign or malignant hyperproliferative epidermal pathology comprising administering nicotinamide and/or cADPR, optionally in combination with a vitamin $D_3$ analog or a vitamin B analog. That application neither teaches nor suggests the use of vitamin $D_3$ agonistic derivatives in the treatment of the cutaneous signs related to aging.

Vitamin $D_3$ and vitamin $D_3$ analogs are known to possess anti-proliferative and prodifferentiating properties and are therefore highly effective in the treatment of hyperproliferative skin disorders, for example psoriasis vulgaris. It would therefore be reasonable for one skilled in the art to expect that an agent exhibiting anti-proliferative activity in keratinocytes would be contraindicated in treating the symptoms observed in skin atrophy. In fact, Fujimura et al. (Fujimura et al, 2000) report that topical application of $1\alpha,25$-dihydroxyvitamin $D_3$ induces skin wrinkling on hairless mice.

The art has neither taught nor suggested the use of specific vitamin $D_3$ analogs alone or in combination with nicotinamide and/or cADPR for the prevention, treatment or attenuation of disorders associated with cutaneous aging.

There remains a yet unmet need for compositions and methods useful in treating the symptoms associated with natural, premature or induced aging.

SUMMARY OF THE INVENTION

The present invention is based on the unexpected observation that vitamin $D_3$ and specific analogs thereof alone or in combination with nicotinic acid and or cADPR are in fact effective in preventing, attenuating and treating the symptoms associated with skin atrophy including loss of elasticity, fine lines, wrinkles and pigmentation. While using preparations according to the present invention to retard hyperproliferative skin lesions such as psoriasis, the inventors surprisingly discovered beneficial effects on normal skin appearance and texture.

Thus, a composition comprising the combination of vitamin $D_3$ or specific analogs thereof with nicotinamide and or cADPR, or analogs or derivatives thereof is unexpectedly effective in preventing, attenuating and treating the symptoms associated with cutaneous aging.

In one aspect the present invention provides a dermatological composition useful for topical administration for preventing, retarding, arresting, or reversing atrophy in mammalian skin comprising as an active ingredient a dermatologically effective amount of at least one active agent selected from the group consisting of vitamin $D_3$ and a vitamin $D_3$ analog; and a dermatologically effective amount of at least one active agent selected from the group consisting of cyclic adenosine diphosphate-ribose (cADPR), a cADPR derivative, a cADPR metabolite, a cADPR agonist, nicotinamide (NA), a nicotinamide agonist, a nicotinamide derivative, a nicotinamide metabolite and prodrugs thereof; and a dermatologically acceptable excipient or carrier.

In some embodiments the vitamin $D_3$ analog comprises the 9,10 secosterol chemical structure. In certain embodiments the vitamin $D_3$ analog is selected from calcitriol and calcipotriol. In specific embodiments the vitamin $D_3$ analog is calcipotriol.

In specific embodiments the composition comprises a dermatologically effective amount of at least one active agent selected from the group consisting of cyclic adenosine diphosphate-ribose (cADPR) and nicotinamide. In some embodiments the composition comprises both NA and cADPR.

In preferred embodiments the mammalian skin is human skin. In certain embodiments atrophy of the skin is associated with steroid-induced atrophy, menopausal induced atrophy or aging.

In specific embodiments the composition consists essentially of a dermatologically effective amount of at least one active agent selected from the group consisting of vitamin $D_3$ a vitamin $D_3$ analog; and a dermatologically effective amount of at least one active agent selected from the group consisting of cyclic adenosine diphosphate-ribose (cADPR), a cADPR derivative, a cADPR metabolite, a cADPR agonist and prodrugs thereof.

In other embodiments the composition consists essentially of a dermatologically effective amount of at least one active agent selected from the group consisting of vitamin $D_3$ and a vitamin $D_3$ analog; and a dermatologically effective amount of at least one active agent selected from the group consisting of nicotinamide, a nicotinamide agonist, a nicotinamide derivative, a nicotinamide metabolite and prodrugs thereof.

In a second aspect the present invention provides a composition useful for topical administration for preventing or treating an epidermal condition related to aging, comprising at least one active agent selected from the group consisting of vitamin $D_3$ and a vitamin $D_3$ analog; a dermatologically effective amount of at least one active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof; and a dermatologically acceptable excipient or carrier.

In some embodiments the vitamin $D_3$ analog comprises the 9,10 secosterol chemical structure. In certain embodiments the vitamin $D_3$ analog is selected from calcitriol and calcipotriol. In specific embodiments the vitamin $D_3$ analog is calcipotriol.

In specific embodiment the composition comprises a dermatologically effective amount of at least one active agent selected from the group consisting of cyclic adenosine diphosphate-ribose (cADPR) and nicotinamide.

In one embodiment the epidermal condition related to aging is associated with chronological aging, photoaging or a combination of chronological aging and photoaging. In specific embodiments the epidermal condition is selected from the group consisting of fine lines, wrinkles, discoloration, sagging, enlarged pores, rough skin, dry skin, acne, alopecia and stretch marks.

In another aspect the present invention provides a dermatological composition useful for topical administration for preventing, retarding, arresting, or reversing atrophy in mammalian skin consisting essentially of a dermatologically effective amount of at least one active agent selected from the group consisting of calcitriol, calcipotriol and mixtures thereof; and a dermatologically acceptable excipient or carrier.

In yet another aspect the present invention provides a dermatological composition useful for topical administration for preventing or treating an epidermal condition related to aging, comprising at least one active agent selected from the group consisting of calcitriol, calcipotriol and mixtures thereof; and a dermatologically acceptable excipient or carrier.

The present invention further provides a composition of the present invention packaged in a container suitable for dispensing of said composition; and written instructions for use.

Hence, according to further aspects of the present invention there are provided pharmaceutical, cosmetic or cosmeceutical kits, which comprise a composition comprising a dermatologically effective amount of an agent selected from the group consisting of vitamin $D_3$ and a vitamin $D_3$ analog; a dermatologically effective amount of at least one active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof; and a dermatologically acceptable excipient or carrier.

The compositions of the present invention may be formulated in a form selected from an aqueous solution, a non-aqueous solution, a lotion, a cream, a gel, an ointment, foam, a mousse, a spray, an emulsion, a microemulsion, and a powder. The compositions may be applied directly to the skin or via an adhesive patch or bandage.

In other aspects, the present invention provides methods for preventing, retarding, arresting, or reversing atrophy an to preventing or treating an epidermal condition related to aging in mammalian skin comprising the step of topically applying the compositions of the invention to the skin.

Accordingly, the present invention provides a method for preventing, retarding, arresting, or reversing atrophy in mammalian skin comprising the step of:

topically applying to the skin a dermatologically effective amount of a composition comprising at least one active agent selected from the group consisting of of vitamin $D_3$ and a vitamin $D_3$ analog; at least one active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof; and a dermatologically acceptable carrier.

In preferred embodiments the mammalian skin is human skin. In certain embodiments atrophy of the skin is associated with steroid-induced atrophy, menopausal induced atrophy or aging. Aging refers to chronological aging, photoaging or a combination of chronological aging and photoaging.

In another aspect the present invention provides a method of preventing or treating an epidermal condition related to aging. The method comprises topically administering to a subject in need thereof a dermatologically effective amount of a composition comprising at least one active agent selected from the group consisting of vitamin $D_3$ and a vitamin $D_3$ analog; a dermatologically effective amount of at least one active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof; and a dermatologically acceptable excipient or carrier.

In specific embodiments the vitamin $D_3$ analog is calcipotriol.

In certain embodiments the composition comprises a dermatologically effective amount of an agent selected from the group consisting of cyclic adenosine diphosphate-ribose (cADPR) and nicotinamide.

In preferred embodiments the subject is a human subject. In one embodiment the epidermal condition related to aging is associated with chronological aging, photoaging or a combination of chronological aging and photoaging. In specific embodiments the epidermal condition is selected from at least one of the group consisting of fine lines, wrinkles, discoloration, sagging, enlarged pores, rough skin, dry skin, acne, alopecia and stretch marks.

In certain embodiments the methods of the invention comprise the step of: topically administering to a subject in need thereof a dermatologically effective amount of a composition consisting essentially of at least one active agent selected from the group consisting of vitamin $D_3$ and a vitamin $D_3$ analog; and at least one active agent selected from the group consisting of cyclic adenosine diphosphate-ribose (cADPR), a cADPR derivative, a cADPR metabolite, a cADPR agonist and prodrugs thereof; and a dermatologically acceptable carrier.

In other embodiments the methods comprise the step of:

topically administering to a subject in need thereof a dermatologically effective amount of a composition consisting essentially of at least one active agent selected from the group consisting of vitamin $D_3$ and a vitamin $D_3$ analog; at least one active agent selected from the group consisting of nicotinamide, a nicotinamide agonist, a nicotinamide derivative, a nicotinamide metabolite and prodrugs thereof; and a dermatologically acceptable excipient or carrier.

In one aspect the present invention provides the use of at least one active agent selected from the group consisting of vitamin $D_3$ and a vitamin $D_3$ analog; and at least one active agent selected from the group consisting of nicotinamide, a nicotinamide agonist, a nicotinamide derivative, a nicotinamide metabolite and prodrugs thereof; for the preparation of a therapeutic or cosmetic composition for topical administration in the treatment of an epidermal condition related to skin atrophy, chronological aging, photoaging or a combination of chronological aging and photoaging.

In another aspect the present invention provides the use of the use of at least one active agent selected from the group consisting of calcitriol and calcipotriol; for the preparation of a therapeutic or cosmetic composition for topical administration in the treatment of an epidermal condition related to skin atrophy, chronological aging, photoaging or a combination of chronological aging and photoaging.

These and other embodiments of the present invention will become apparent in conjunction with the figures, description and claims that follow.

DETAILED DESCRIPTION OF THE INVENTION

Figure 1A:
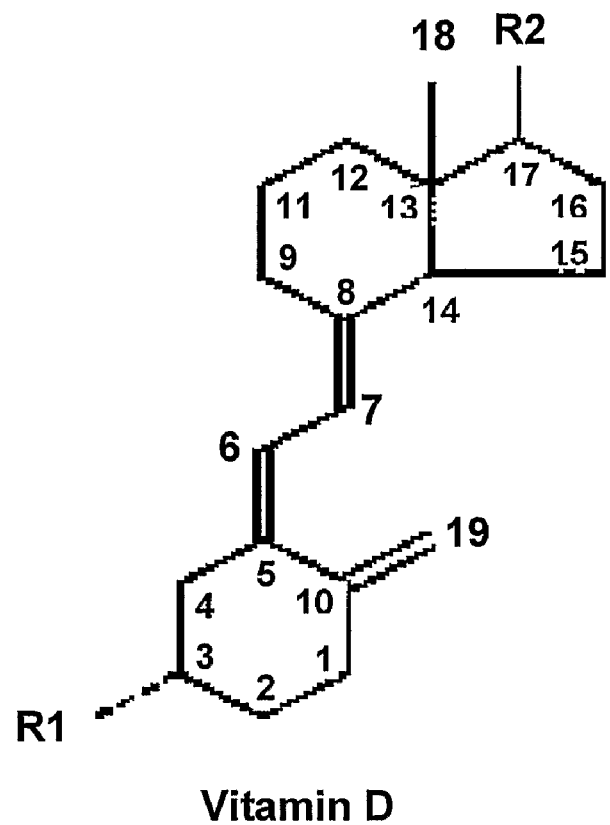
FIG. 1A shows the 9,10 secosterol structure of vitamin D and side chain of vitamin $D_3$.

The present invention relates to pharmaceutical, cosmetic or cosmeceutical compositions, kits and methods, which can be used in the treatment of skin disorders related to skin atrophy and aging, including the diminution of fine lines, wrinkles, discoloration and stretch marks. The principles and operation of the compositions and methods according to the present invention may be better understood with reference to the drawings and accompanying descriptions.

Vitamins D and vitamin D analogs have been shown to possess anti-proliferative activity and further enhance the antiproliferative activity of nicotinamide and nicotinamide derivatives. The present invention now discloses the unexpected, beneficial and beautifying effects of compositions comprising a combination of vitamin $D_3$ and vitamin $D_3$ analogs and an active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof. These compositions are effective in preventing, attenuating and treating skin atrophy.

It was unexpectedly found that vitamin $D_3$ and vitamin $D_3$ analogs in combination with other active agents including nicotinamide and or cADPR and derivatives thereof, having synergistically anti-proliferative effects in preventing and reducing the appearance of the symptoms associated with skin atrophy, chronologically aged skin and photoaged skin.

As a person ages, the skin undergoes significant changes:

The cells divide more slowly, and the inner layer of skin (the dermis) starts to thin. Fat cells beneath the dermis begin to atrophy. The underlying network of elastin and collagen fibers, which provides scaffolding for the surface skin layers, loosens and unravels leading to the loss of elasticity and to the concomitant sags and furrows.

The sweat- and oil-secreting glands atrophy, depriving the skin of their protective water-lipid emulsions. The skin's ability to retain moisture diminishes and it becomes dry and scaly.

Frown lines between the eyebrows and crow's feet, which radiate from the corners of the eyes, appear to develop because of permanent small muscle contractions. Other lines may form from habitual facial expressions. Gravity exacerbates the situation, contributing to the formation of jowls and drooping eyelids.

Ultraviolet radiation plays a pivotal role as a cause of prematurely aging skin (called photoaging) and skin cancers. Overall, exposure to ultraviolet (referred to as UVA or UVB) radiation emanating from sunlight accounts for about 90% of the symptoms of premature skin aging, and most of these effects occur by age 20. Even small amounts of UV radiation trigger process leading to skin wrinkles.

Long-term repetitive and cumulative exposure to sunlight appears to be responsible for the vast majority of undesirable consequences of aging skin, including basal cell and squamous cell carcinomas.

Both UVA and UVB rays cause damage leading to wrinkles, lower immunity against infection, aging skin disorders, and cancer. They appear to damage cells in different ways, however.

UVB is the primary agent responsible for sunburning. UVB is most intense at midday when sunlight is brightest. UVA penetrates more deeply and efficiently, however. The intensity of UVA tends to be less variable both during the day and throughout the year than UVB. For example, only about half of the yearly UVA dose is received during the summer months and the balance is spread over the rest of the year. UVA is also not filtered through window glass. Both UVA and UVB rays cause damage, including skin damage.

Even small amounts of UV radiation trigger the process that can cause wrinkles. Sun damages collagen fibers, the major structural protein in the skin, and causes accumulation of abnormal elastin. In response to this sun-induced elastin accumulation, large amounts of enzymes called metalloproteases are produced.

While the normal function of metalloproteases is to remodel the sun-injured tissue by manufacturing and reforming collagen, some metalloproteases produced by sunlight actually degrade collagen. The result is an uneven matrix of disorganized collagen fibers called solar scars. Repetition of this imperfect skin rebuilding over and over again causes wrinkles.

Another significant event the wrinkling process is the overproduction of free radicals. Without wishing to be bound to theory, oxidation and oxidative stress may specifically contribute to wrinkling by activating the specific metalloproteases that degrade connective tissue.

In addition to sunlight, other factors may hasten the formation of wrinkles:

Cigarette Smoke: Smoking produces oxygen-free radicals, which are known to accelerate wrinkling and aging skin disorders and increase the risk for nonmelanoma skin cancers. Studies also suggest that smoking and subsequent oxidation produce higher levels of metalloproteases;

Air Pollution: Ozone might be responsible for vitamin E depletion in the skin;

Rapid Weight Loss: The volume of fat cells that cushion the face may be reduced if weight loss occurs too rapidly, and can cause the skin to sag.

DEFINITIONS

For convenience and clarity certain terms employed in the specification, examples and claims are described herein.

As is described hereinabove, vitamin $D_3$ and its analogs are known as useful agents in the treatment of psoriasis and other inflammatory skin diseases (Morimoto et al., 1986). However, the anti-aging effect exerted by a vitamin $D_3$ metabolite in combination with an active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof has never been observed hitherto.

The vitamin $D_3$ analog, according to the present invention, is any analog of vitamin $D_3$, such as, but not limited to, a vitamin $D_3$ metabolite, a vitamin $D_3$ agonist and a vitamin $D_3$ derivative. The vitamin $D_3$ agent can further be a prodrug of each of the above agents. Preferably the vitamin $D_3$ analog comprises the 9,10 secosterol structure.

Figure 1A:
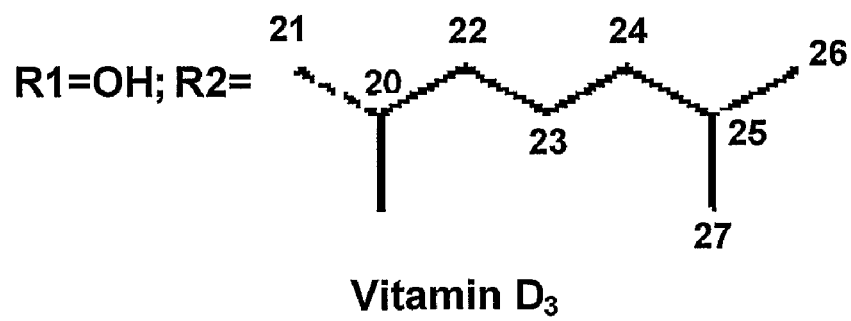
Figure 1B:
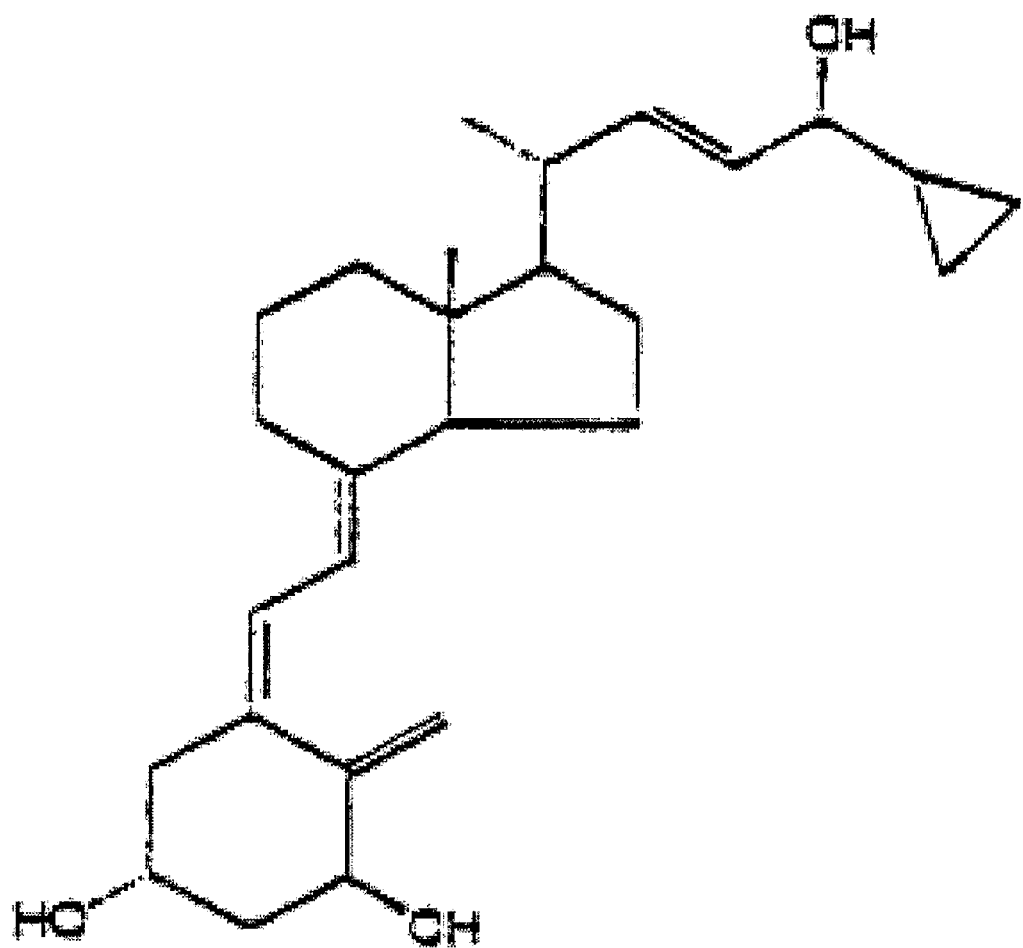
FIG. 1B shows the chemical structure of calcipotriol.

FIG. 1 shows the 9,10 secosterol chemical structure associated with vitamin D, and the residues R1 and R2 of vitamin $D_3$.

According to certain embodiment the analogs of vitamin $D_3$ are selected from cholecalciferol, calcifediol, calcitriol and calcipotriol. In some embodiments the vitamin $D_3$ is selected from calcitriol and calcipotriol. In specific embodiments the vitamin $D_3$ is calcipotriol.

As used herein, the phrase "effective amount" and "dermatologically effective amount" describes an amount of the agent that is sufficient to substantially abrogate, substantially inhibit, slow or reverse the progression of skin atrophy or the appearance of epidermal symptoms associated with aging.

An "active agent" refers to a compound that when used per se or in combination with one or more compounds is able to substantially abrogate, substantially inhibit, slow or reverse the progression of skin atrophy or the appearance of epidermal symptoms associated with aging; for example improvement of skin appearance and texture.

A dermatologically effective amount of a composition comprising at least one active agent selected from the group consisting of vitamin $D_3$ and a vitamin $D_3$ analog relates to a unit dose of the composition comprising about 0.0001% to about 1% vitamin $D_3$ and or a vitamin $D_3$ analog. In specific embodiments vitamin $D_3$ and a vitamin $D_3$ are present in the composition in a unit dose of the composition comprising about 0.001% to about 0.1%.

According to the present invention, final concentrations of the vitamin $D_3$ metabolite typically range between 0.2 μM and 200 μM, and more preferably between about 1.0 μM and about 100 μM. The effective concentration of the vitamin $D_3$ and analogs is preferably between about 0.1 μg to about 100

μg per gram dosage unit in a dosage unit form, preferably about 5 μg to about 50 μg per gram dosage unit in a dosage unit form.

As used herein, "skin atrophy" means the thinning and/or general degradation of the dermis often characterized by a decrease in collagen and/or elastin as well as decreased number and size of fibroblast cells. Skin atrophy is a natural result of menopause, chronological aging and of photoaging and often is an undesirable side effect resulting from corticosteroid treatment. Menopause may be physiological menopause or surgery- or treatment-induced menopause.

Herein, the term "treating" includes abrogating, substantially inhibiting, slowing or reversing the progression, substantially ameliorating clinical symptoms, or substantially preventing the appearance of symptoms associated with aging and skin atrophy. The term "treating" further is meant to include improvement of skin appearance and texture, hydrating, healing or smoothing of the skin. The symptoms include but are not limited to fine lines, wrinkling, age spots and other discolorations of the skin, sagging skin, growths, dry skin, rough skin, dull skin, acne, alopecia and stretch marks.

The treatment of a condition such as skin atrophy or aging of the epidermal cells includes, according to the present invention, treatment of the symptoms described hereinabove with respect to aging of epidermal cells. This treatment further includes prevention of these symptoms, and in particular aging signs, before they occur.

The present invention includes compositions further comprising a dermatologically effective amount of an agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof.

A suitable nicotinamide agent is either nicotinamide itself, or any nicotinamide analog that is known to act similarly thereto, such as, but not limited to, a nicotinamide agonist, a nicotinamide derivative or a nicotinamide metabolite. The nicotinamide agent can further be a prodrug of each of the nicotinamide agents described.

In certain embodiments the effective amount of nicotinamide ranges between about 1 mM and about 50 mM. In specific embodiments the effective amount of nicotinamide ranges between about 1 mM and about 30 mM and preferably between about 5 mM and about 25 mM. The effective concentration of NA or NA analog is about 0.1 mg and 6 mg per gram dosage unit in a dosage unit form, and preferably from about 0.1 mg and 3 mg per gram dosage unit in a dosage unit form, and more preferably from about 0.5 mg to about 2.5 mg per gram dosage unit in a dosage unit form.

Similarly, the cADPR agent is either cADPR itself or any cADPR analog that is known to act similarly thereto, such as, but not limited to, a cADPR agonist, a cADPR derivative or a cADPR metabolite. The cADPR agent can further be a prodrug of each of the cADPR agents described. In certain embodiments the dermatologically effective amount of cADPR, according to the present invention, ranges between about 1 μM and 100 μM. In certain embodiments the effective amount of cADPR in the composition of the present invention ranges from about 10 μM and about 50 μM and preferably between about 25 μM and about 50 μM. The effective concentration is preferably between about 0.5 μg to about 55 μg per gram dosage unit in a dosage unit form, preferably about 5 μg to about 27 μg per gram dosage unit in a dosage unit form, and preferably from about 13 μg to about 27 μg/g.

The present invention encompasses compositions consisting essentially of a dermatologically effective amount of vitamin $D_3$ analog selected from calcitriol and calcipotriol and a dermatologically effective amount of an agent selected from the group consisting of cyclic adenosine diphosphate-ribose (cADPR), a cADPR derivative, a cADPR metabolite, a cADPR agonist and pro drugs thereof.

The present invention further encompasses compositions of the present invention consists essentially of a dermatologically effective amount of vitamin $D_3$ analog selected from calcitriol and calcipotriol and a dermatologically effective amount of an agent selected from the group consisting of nicotinamide, a nicotinamide agonist, a nicotinamide derivative, a nicotinamide metabolite and prodrugs thereof.

A preferred pharmaceutical, cosmetic or cosmeceutical composition according to the present invention therefore comprises a vitamin D analog at a final concentration that ranges between about 10 μM and 100 μM nicotinamide at a final concentration that ranges between about 10 mM and about 50 mM and cADPR at a final concentration that ranges between about 25 μM and about 50 μM; and a dermatologically acceptable carrier.

Preferably, the vitamin D3 metabolite is 1α,25 dihydroxyvitamin $D_3$.

As used herein, the phrase "dermatologically acceptable carrier" refers to a carrier or a diluent that does not cause significant irritation to the skin and does not abrogate the biological activity and properties of the applied active agent.

Examples of dermatologically acceptable carriers that are useful in the context of the present invention include, without limitation, emulsions, creams, aqueous solutions, oils, ointments, pastes, gels, lotions, milks, foams, suspensions and powders.

The dermatologically acceptable carrier of the present invention may include, for example, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment or mixtures thereof.

Therefore, the composition of the present invention may be, for example, in the form of an oil, a gel, a solid stick, a lotion, a cream, a milk, an aerosol, a spray, a foam, a mousse, an ointment or a fatty ointment or a powder.

Preferably, the compositions of the present invention are administered topically.

The compositions of the present invention may be manufactured by processes well known in the art, e.g., by means of conventional mixing, dissolving, granulating, dragger-making, levigating, emulsifying, encapsulating, entrapping or lyophilizing processes.

The compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Formulations

The therapeutic or cosmetic compositions of the invention comprise a dermatologically or cosmetically acceptable carrier to act as a diluent, dispersant or vehicle for vitamin D, so as to facilitate its distribution when the composition is applied to the skin. Vehicles other than, or in addition to, water include liquid or solid emollients, solvents, humectants, thickeners and powders. The present invention may be formulated for topical administration in the form of aqueous or non-aqueous solutions, lotions, creams, gels, ointments, foam, mousse, sprays, emulsions, microemulsions, adhesive patches, powders etc. The formulation may be oleaginous-based, occlusive composition comprising, for example, white petroleum and or mineral oil. In some embodiments the composition is non-greasy or substantially non-greasy and can be water-based formulations.

For the formulations, the effective concentration of the vitamin $D_3$ and analogs is preferably between about 0.1 μg to about 100 μg per gram dosage unit in a dosage unit form, preferably about 5 μg to about 50 μg per gram dosage unit in a dosage unit form; the effective concentration of NA or NA analog is about 0.1 mg and 6 mg per gram dosage unit in a dosage unit form, and preferably from about 0.1 mg and 3 mg per gram dosage unit in a dosage unit form, and more preferably from about 0.5 mg to about 3 mg per gram dosage unit in a dosage unit form; and the effective concentration is preferably between about 0.5 μg to about 55 μg per gram dosage unit in a dosage unit form, preferably about 5 μg to about 27 μg per gram dosage unit in a dosage unit form, and preferably from about 13 μg to about 27 μg/g.

Non-limiting examples of suitable topical formulations are as follows:

Lotions and Creams

The lotions contain an effective concentration of one or more compounds selected from vitamin D and a vitamin D analog and an active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof.

The compositions of the present invention may also include at least one or more emollient, which can function as either or both a lubricating and thickening agent. The emollients can comprise in total from about 0.1% to about 50%, preferably from about 1% to about 10%, by weight of the composition. Any emollients known to those of skill in the art as suitable for application to human skin may be used. These include, but are not limited to: hydrocarbon oils and waxes, including mineral oil, petrolatum, paraffin, ceresin, ozokerite, microcrystalline wax, polyethylene, and perhydrosqualene; silicone oils; triglyceride fats and oils, including those derived from vegetable, animal and marine source; including jojoba oil and shea butter; acetoglyceride esters, such as acetylated monoglycerides; ethoxylated glycerides, such as ethoxylated glyceryl monostearate; fatty acids, fatty alcohols and derivatives thereof. Other suitable emollients include lanolin and lanolin derivatives; polyhydric alcohols and polyether derivatives; polyhydric alcohol esters; wax esters; vegetable waxes; phospholipids, such as lecithin and derivatives; sterols, including, but not limited to, cholesterol and cholesterol fatty acid esters; amides, such as fatty acid amides, ethoxylated fatty acid amides, and solid fatty acid alkanolamides.

The lotions may further contain from about 1% to about 10%, more preferably from 2% to 5%, of an emulsifier. The emulsifiers can be nonionic, anionic, cationic or a mixture thereof. Suitable emulsifiers are known to those with skill in the art.

Other conventional components of such lotions and creams may be included. One such additive is a thickening agent at a level from 1% to 10% of the composition. Examples of suitable thickening agents include, but are not limited to: crosslinked carboxypolymethylene polymers, ethyl cellulose, polyethylene glycols, gum tragacanth, gum karaya, xanthan gums, bentonite and other clays, hydroxyethyl cellulose, and hydroxypropyl cellulose.

The lotions and creams are formulated by simply admixing all of the components together. Preferably the vitamin D or vitamin D analog is dissolved, suspended or otherwise uniformly dispersed in the mixture.

Solutions and Suspensions

The solutions, which may be aqueous or non-aqueous, are formulated to contain an effective concentration of one or more compounds selected from vitamin D and a vitamin D analog and an active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof.

The effective concentration of the vitamin $D_3$ analog is preferably between about 0.1 μg to about 100 μg per gram dosage unit in a dosage unit form, preferably about 5 μg to about 50 μg per gram dosage unit in a dosage unit form. Suitable organic materials useful as the solvent or a part of a solvent system are as follows: propylene glycol, polyethylene glycol, polypropylene glycol, glycerin, sorbitol esters, 1,2,6-hexanetriol, ethanol, isopropanol, diethyl tartrate, butanediol, and mixtures thereof. Such solvent systems can also contain water.

When the compositions of the invention are formulated as an emulsion, the proportion of the fatty phase may range from about 5% to about 80% by weight, and preferably from about 5% to about 50% by weight, relative to the total weight of the composition. Oils, emulsifiers and co-emulsifiers incorporated in the composition in emulsion form are selected from among those known to those with skill in the cosmetic or dermatological field.

Gels and Solids

Gel compositions can be formulated by simply admixing a suitable thickening agent to the previously described solution or suspension compositions. Examples of suitable thickening agents have been previously described with respect to the lotions.

The gelled compositions contain an effective concentration of at least one compound selected from vitamin D and a vitamin D analog and an active agent selected from the group consisting of cyclic adenosine diphosphate-ribose (cADPR), a cADPR derivative, a cADPR metabolite, a cADPR agonist, nicotinamide, a nicotinamide agonist, a nicotinamide derivative, a nicotinamide metabolite and prodrugs thereof.

The composition further comprises from about 5% to about 75% of an organic solvent as previously described; from about 0.5% to about 20% of a thickening agent, and the balance being water or other aqueous carrier.

Compositions of solid forms may be formulated as stick-type compositions intended for application to the lips or other parts of the body. Such compositions contain an effective amount of at least one compound selected from vitamin D and a vitamin D analog. The solids also contain from about 50% to about 98% of the previously described emollients. This composition can further contain from about 1% to about 20%, of a suitable thickening agent, and, if desired or needed, emulsifiers and water or buffers. Thickening agents previously described with respect to lotions are suitably employed in the compositions in solid form.

Other ingredients, such as preservatives, including methylparaben or ethyl-paraben, perfumes, dyes or the like, that are known in the art to provide desirable stability, fragrance or color, or other desirable properties, to compositions for application to the skin.

The preparation of the present invention is effective to prevent and treat skin disorders associated with aging including the reduction in skin elasticity, generation of wrinkles and discoloration, and skin sagging due to cutaneous aging caused by normal and photoaging.

The compositions formulated as solutions or suspensions may be applied directly to the skin, or, may be formulated as an aerosol and applied to the skin as a spray, foam or mousse. The aerosol compositions further contain from about 20% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as known in the art in a quantity and under a pressure suitable to expel the contents of the container. In the case of a pressurized aerosol, the dosage unit may be determined by providing a valve to deliver a metered amount.

In other embodiments the compositions formulated as solutions, suspensions lotions and gels of the present invention are formulated as a foam or mousse for dermal application. Relevant carriers for formulation as a foam or mousse are taught, for example, in International Patent Application Publication No. WO2004/037225 and U.S. Pat. No. 6,730,288.

Additives

For any agent or combination of agents used within the scope of the invention, the dermatologically effective amount or dose can be estimated initially from cell culture assays. For example, a dose can be formulated in animal models to achieve a circulating concentration range that includes the $IC_{50}$ as determined in cell culture (e.g., the concentration of the test compound, which achieves a half-maximal inhibition of the epidermal cells proliferation). Such information can be used to more accurately determine useful doses in humans.

Other examples of additives include sunscreens and tanning agents. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are also known as parsol MCX and benzophenone-3, respectively. The amount of sunscreen employed in the compositions can vary depending upon the degree of UV radiation protection desired. The sunscreen must be compatible with the active compound but in general the composition may comprise from about 1% to about 20%, of a sunscreen. Exact amounts will vary depending upon the sunscreen chosen and the desired Sun Protection Factor (SPF).

The composition of the present invention may further comprise an anti-oxidant/radical scavenger. The inclusion of an anti-oxidant/radical scavenger increases the benefits of the composition. The anti-oxidant/radical scavenger may be added to the compositions of the present invention in a concentration range of about 0.1% to about 10% total weight of the composition. Anti-oxidants/radical scavengers include ascorbic acid (vitamin C) and its salts, and tocopherol (vitamin E).

Certain vitamin A metabolites, as well as agonists, derivatives and prodrugs of vitamin A, other than retinol and retinoid derivatives, may be incorporated into the compositions of the present invention. Examples of other vitamin A agents that are useful in the context of the present invention include, without limitation, the well-known variety of retinoic acid receptor (RAR) agonists. These include, without limitation, chromans, thiochromans, tetrahydroquinolines, substituted tetrahydronaphthalenes, substituted dihydronaphthalenes, trisubstituted phenyls, aromatic tetracyclic compounds, substituted cyclohexanes, substituted cyclohexenes, substituted cyclohexanedienoic acids, substituted adamantanes, substituted diaryl and heteroaryl compounds and many more.

Vitamin C, or ascorbic acid is a very potent antioxidant and may even be protective against UVA and UVB rays. Studies suggest that topical vitamin E, particularly alpha tocopherol (a form of vitamin E) cream decreased skin roughness, length of facial lines, and wrinkle depth. Studies on mice have also reported reductions in UV-induced skin cancer with its use. Vitamin K may also be useful for treating capillary damage.

Green and black tea and extracts thereof are suitable as additives. Other plant derived agents include pomegranate and soy extracts, aloe, ginger, grape seed extract, and coral extracts.

Certain copper containing compounds may both protect skin and help repair it. Of note, copper itself is a toxic metal and it should only be used in products that contain that bind to copper. Most studies have been conducted on a copper peptide glycyl-1-histidyl-1-lysine:copper (II) or GHK-Cu.

Color correctors are suitable additives and may be desired when blemishes are prominent. For example, green neutralizers mask red lesions; yellow camouflages dark circles and bruises; and white helps to minimize wrinkles.

Other additives including glycosaminoglycans, such as hyaluronic acid and the like.

Product Packaging and Kits

In use, a small quantity of the composition, for example from about 0.1 ml to about 100 ml, is applied to exposed areas of the skin, from a suitable container or applicator and, if necessary, it is then spread over and/or rubbed into the skin using the hand, fingers or a suitable device. The product may be specifically formulated for use as a hand or facial treatment.

When formulated the composition can be packaged in a suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a dermatologically or cosmetically acceptable composition as herein defined. The shape of the container is not limited in this invention, and can be a tube, a pump dispenser, a compressed dispenser, a bottle, a spray, a sachet or the like.

Many of the agents in the claimed compositions of the present invention may be provided as physiologically acceptable salts wherein the agent may form the negatively or the positively charged species. Examples of salts in which the agent forms the positively charged moiety include, without limitation, quaternary ammonium (defined elsewhere herein), salts such as the hydrochloride, sulfate, carbonate, lactate, tartrate, maleate, succinate, and the like, wherein the nitrogen of the quaternary ammonium group is a nitrogen of a compound of the present invention which reacts with an appropriate acid. Salts in which the agent forms the negatively charged species include, without limitation, the sodium, potassium, calcium and magnesium salts formed by the reaction of a carboxylic acid group in the molecule with the appropriate base (e.g., sodium hydroxide (NaOH), potassium hydroxide (KOH), calcium hydroxide ($Ca(OH)_2$), etc.).

The compositions of the present invention may, if desired, be presented in a pack or dispenser device, such as a regulatory agency approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of the compositions, which notice is reflective of approval by the agency of the form of the compositions or human or veterinary administration. In other embodiments the compositions are prepared for over the counter (OTC) use and sale.

Compositions comprising the agents of the invention formulated in a compatible carrier may also be prepared, placed in an appropriate container, and labeled for prevention and treatment of a skin disorders associated with aging.

Hence, according to further aspects of the present invention, there are provided cosmetic and cosmeceutical kits. The cosmetic and cosmeceutical kits of the present invention comprise any of the agents or combinations of agents described hereinabove.

As is discussed hereinabove and is further demonstrated in the Examples section that follows, the high efficacy of the agents or the combinations of agents of the present invention in treating skin disorders associated with chronological aging and photoaging became apparent despite the capability of these agents or combination of agents to inhibit the proliferation of epidermal cells.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

The following examples are to be considered merely as illustrative and non-limiting in nature. It will be apparent to one skilled in the art to which the present invention pertains that many modifications, permutations, and variations may be made without departing from the scope of the invention.

Example 1

In Vitro Assays

Cell Culture

The antiproliferative activity of vitamin $D_3$, nicotinamide and cADPR and their derivatives and analogs was tested in two model systems: (i) a spontaneously immortalized human keratinocyte, which is referred to herein as "HaCat cell line" or "HaCat cells", and serves as a model for highly proliferative epidermis, such as, but not limited to, psoriatic epidermis (Okenfels et al, 1995), and as a model for effects of external modulators of epidermal differentiation (Paramio, et al, 1997)

The antiproliferative effects of these compounds were further demonstrated on rapidly proliferating human keratinocytes, which are referred to herein as "cultured human epidermal keratinocytes", and serves as model for detecting antiproliferative agents in the treatment of psoriasis (Nikoloff et al., 1988).

These models can be used, according to the present invention, to test the antiproliferative efficacy of agents described herein, including their derivatives, metabolites, agonists and prodrugs. The immortalized human keratinocyte HaCat cells are routinely cultured in 75 cm² flasks using Eagle's minimal essential medium (MEM-EAGLE) supplemented with 5% fetal calf serum (FCS) and 1% antibiotics (penicillin 20 units/ml; streptomycin 20 μg/ml and nystatin 2.5 units/ml) at 37° C. in 95% air/5% $CO_2$. The medium is replaced every 3-4 days.

Long-term cultures of HaCat cells grown with vitamin D or vitamin D derivatives are obtained by cultivating HaCat cells, for 6 months, in routinely used medium, supplemented with 10 mM or 20 mM vitamin D.

Other long-term cultures of cells with other agents are similarly obtained by cultivating HaCat cells, for a prolonged period of time, in routinely used medium supplemented with combinations of NA and cADPR, vitamin D and vitamin A.

Human Epidermal Keratinocytes (passages 3-6), obtained from normal face-lift surgery, are cultivated in serum-free KGM®-2 BulletKit® (Clonetics, USA) medium with low calcium for accelerated proliferation of the keratinocytes.

Reagents:

Nicotinamide (NA); cyclic adenosine diphosphate-ribose (cADPR); calcitriol (1α,25-dihydroxy-vitamin D3); 3-(4,5-dimethylthiazol-2-yl)-2,5-diphenyltetrazolium bromide (MTT); propidium iodide; dimethylsulphoxide (DMSO); bovine serum albumin (BSA); sucrose; trisodium citrate; igepal CA-630 (NP-40); Tris-(hydroxymethyl)-aminomethane; trypsin; trypsin inhibitor; ribonuclease A; spermin-tetrahydrochloride; sodium dodecylsulfate (SDS); β-mercaptoethanol and hydrogen peroxide ($H_2O_2$), were all obtained from Sigma (USA).

Eagle's minimal essential medium (MEM-EAGLE); DMEM; antibiotics; fetal calf serum (FCS); L-glutamine; Dulbecco's phosphate buffered saline (PBS); and trypsin 0.05%-EDTA solution were obtained from Biological Industries (Israel).

Keratinocyte Growth Medium®-2 Bullet Kit® CC-3107 (for accelerated proliferation) was received from BioWhittaker, Inc. (A Cambrex Company, Clonetics, USA).

Anti-human cytokeratin 10 (NCL-CK10) and involucrin (NCL-INV) mouse monoclonal antibodies were obtained from Novocastra Laboratories Ltd. (UK) and CY™ 2-conjugated goat anti-mouse IgG was obtained from Jackson Immunoresearch Laboratories, Inc. (USA).

HaCat cells were propagated in 25 cm² or 75 cm² tissue culture flasks (Corning, USA) and 24-well and 96-well tissue culture plates (Corning, USA) were used for incubation of the cells with different doses of NA (1-50 mM/l), cADPR (1-50 μM), vitamin $D_3$ (1-10000 nM).

Proliferation Assays (MTT Method)

The viability and/or proliferation of HaCat cells and Cultured Human Epidermal Keratinocytes, following treatment with various concentrations of vitamin D, nicotinamide (NA) and/or various concentrations of cADPR and derivatives thereof are determined by the MTT assay, according manufacturer in 96-well microtiter plates.

In brief, an equal number of cells are seeded in each well and incubated for 24 hours. NA or a combination of NA and another agent (NA and cADPR; NA and vitamin D3 metabolite; NA with Vitamin A metabolite), in various concentrations, was added thereafter and the wells were incubated for additional 72 hours. Twenty microliters (20 μl) of 5 mg/ml MTT in phosphate buffered saline (PBS) without $Ca^{+2}$ and $Mg^{+2}$ are then added to each well. The plates are placed in an incubator where MTT converts to the insoluble MTT-formazan crystals by mitochondrial dehydrogenases during about 3.5 hours. The medium is then removed and the obtained formazan crystals are dissolved in 0.2 ml of DMSO. The amount of formazan was quantified in an ELISA-reader at 550 nm. Background values at 650 nm were subtracted. The experiments are performed in triplicate.

Differentiation Assays

Cornified Envelope Formation:

Late differentiation processes in HaCat cells treated with vitamin D or derivatives thereof are measured by determining the cornified cell envelope formation, according to the procedure described in Sun and Green, H, 1976).

In brief, cells are seeded in 24-well tissue culture plates and after attachment (24 hours) are exposed to various concentrations of NA (0, 5, 10, 15 and 20 mM) for 96 hours. The cells are thereafter detached and re-suspended in medium. Counting of total and basal (small, rounded) cells is performed using hemocytometer in tetraplicate aliquots. The remaining cells were spun down, treated with 10 mM Tris-HCl (pH 7.4) supplemented with 1% β-mercaptoethanol and 1% SDS for 10 minutes and cornified envelope cells are counted in tetraplicate aliquots using hemocytometer. The presented data were results of three independent experiments.

Indirect Immunofluorescence:

Effects of vitamin D on early (keratin k10 expression) and late (involucrin expression) differentiation processes in HaCat cells were estimated by indirect immunofluorescence.

In brief, $2 \times 10^4$ cells/ml were seeded on glass coverslips into Petri dishes with 0, 5, 10 and 20 mM vitamin D or calcipotriol. After 72 hours of incubation, cells on the glass coverslips were washed with PBS, fixed by ice-cold mixture of methanol: acetone (1:1) and incubated at −20° C. for 10 minutes. Fixed cells were thereafter washed in PBS and incubated with blocking buffer (1% BSA in PBS) for 10 minutes, to minimize non-specific absorption of the primary antibodies to the coverslips. Thereafter, the cells were incubated for 1 hour with primary monoclonal antibodies (Keratin 10 expression was detected by antihuman mouse monoclonal antibody, at 1/50 final dilution; Involucrin expression was detected by antihuman involucrin mouse monoclonal antibody at 1/100 final dilution), at 37° C. hour in a humidified chamber. Exhaustive, PBS-washed cells were incubated with fluorophor conjugated goat anti-mouse IgG, at 1/50 final dilution, for 30 minutes at room temperature. The slides were viewed under Zeiss microscope (Axioskop-2) equipped with epifluorescence optics and the appropriate filters to avoid cross-channel contamination. The level of keratin 10 and involucrin expression was estimated by counting the positive cells relative to the total cell number. In each slide, at least 500-1000 cells were scored. The presented data is a mean of three independent experiments.

Statistical Analysis

Results are presented as mean±standard deviation of the mean (mean±SD). Statistical significance (P<0.05) was derived by Student's t-test.

Results

Figure 2A:
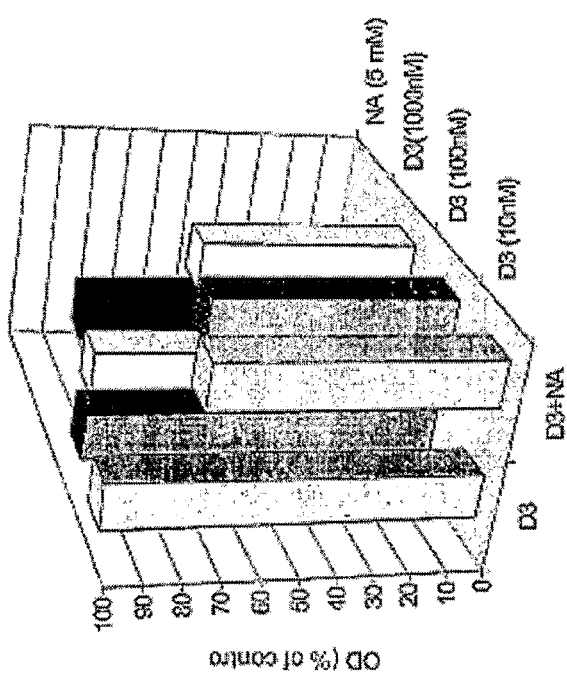
FIGS. 2a and 2b show the anti-proliferative effect of a combination of NA and a calcitriol ($1\alpha25(OH)_2D_3$) on HaCat cell line proliferation (FIG. 2a) and the synergistic effect of this combination as compared with the anti-proliferative effects of each of these compounds separately (NA and $1\alpha25(OH)_2D3$), on this cell line, shown as the effect of the combined treatment minus the effect of each of the compounds (FIG. 2b).
Figure 2B:
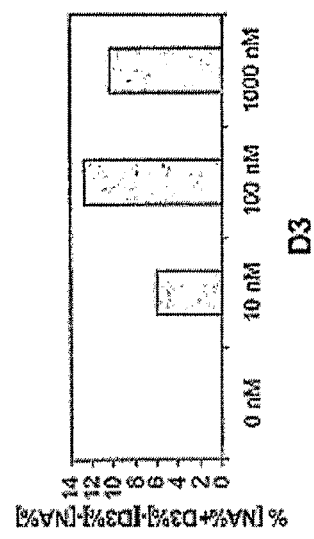

FIG. 2a presents the results obtained with the vitamin $D_3$ and nicotinamide in the HaCat cell line. FIG. 2b presents a deduction of the anti-proliferative effects of $1\alpha25(OH)_2D_3$ and NA, when applied separately on the cell lines as described hereinabove, from the anti-proliferative effect of the combination of NA and $1\alpha25(OH)_2D_3$, presented in FIG. 2a.

As is shown in FIG. 2b the anti-proliferative effect of the combination of NA and $1\alpha25(OH)_2D_3$ is substantially higher than the summation of the anti-proliferative effects of each of these compounds separately. When a combination of 100 nM $1\alpha25(OH)_2D_3$ and 5 mM NA was used in HaCat cells, enhancement of 12% was observed in the inhibition of cell proliferation. These results clearly demonstrate the synergistic effect of a combination of NA and a vitamin $D_3$ metabolite in inhibiting epidermal cell proliferation. In view of these results, the observation that a composition comprising NA and a vitamin $D_3$ analog is useful in treating the signs of cutaneous aging is unexpected.

Example 2

Formulations

The formulations consist essentially of about 0.1 μg/g to about 100 μg/g calcipotriol alone or with about 0.5 mg/g to about 3 mg/g NA; and/or about 5 μg/g to about 27 μg/g cADPR. Exemplary, but not limiting, formulations of the present invention are as follows (W/W (g/100 g) unless otherwise denoted:

| | |
|---|---|
| Carbopol ® | 0.3 |
| Propylene glycol | 2.0 |
| Glycerin | 1.0 |
| White petroleum jelly | 1.5 |
| Cyclomethicone | 6.0 |
| Cetyl alcohol | 0.5 |
| Lubrajel | 10.0 |
| Triethanolamine | 0.3 |
| Calcipotriol | 0.005 |
| Nicotinamide (optional) | 0.21 |
| cADPR (optional) | 0.0013 |
| Water and excipients to | 100 g |
| Steareth-20 | 2.4 |
| Steareth-2 | 2.6 |
| Prostearyl 15 | 8.0 |
| Beeswax | 0.5 |
| Abil ® ZP 2434 | 3.0 |
| Propylene glycol | 3.0 |
| Carbopol ® 941 | 0.25 |
| Triethanolamine | 0.25 |
| Calcipotriol | 0.005 |
| Nicotinamide (optional) | 0.21 |
| cADPR (optional) | 0.0013 |
| Water, excipients to | 100 g |
| White petroleum | 5-50 |
| Mineral oil | 10-50 |
| Lanolin | 0-5 |
| Vitamin E | 0-0.5 |
| Stearyl Alcolhol | 1-15 |
| Steareth-2 | 0-10 |
| Steareth-20 | 1-5 |
| EDTA | 0-0.5 |
| Calcipotriol | 0.005 |
| Nicotinamide (optional) | 0.21 |
| cADPR (optional) | 0.0013 |
| Water, excipients to | 100 g |

Example 3

In Vivo Animal Models

Animal models which mimic human skin disorders such as atrophy and aging are useful in testing compounds for their efficacy in preventing and treating said disorders.

Senescence-accelerated mice (SAM) were established as a group of related inbred strains that have been used as animal models for accelerated senescence and age-associated disorders (Takeda et al., 1981). To analyze the characteristics of skin in SAM, various studies have examined its morphology at the histological and ultrastructural levels (Luo et al., 2002). Histological comparison of skin from senescence-accelerated-prone (SAM P10) and -resistant (SAM R1) mice revealed that the most characteristic features of SAM P10 were remarkable increases in the number of mast cells and in the density of collagen fibers in the dermis. The collagen bundles are disorganized, and various diameters of collagen fibers were observed. The proliferative capacity of fibroblasts in the skin of SAM P10 was reduced in comparison with SAM R1. The SAM P10 mouse is a useful animal model of aged human skin, because of its many similar morphological features, including the reduction of the cutaneous allergic response, and its decreased fibroblast proliferation.

Chiba (Chiba et al., 2003) has developed a useful mouse model for the study of skin aging, particularly with regard to collagen content based on the topical application of squalene monohydroperoxides (Sq-OOH), on the skin of hairless mice. Sq-OOH-treated hairless mice provide a useful model for the study of skin aging, particularly with regard to collagen content.

Repeated topical application of 10 mM Sq-OOH to hairless mice for 15 weeks induces definite skin wrinkling. Image analysis was used to compare wrinkle formation induced by ultraviolet B (UVB) irradiation and Sq-OOH treatment, and the degree of wrinkling in exposed skin was seen to be similar. However, biochemical analysis revealed a significant decrease in collagen content per unit area and mass in Sq-OOH-treated skin, whereas no changes per unit area and decrease in collagen per unit mass were observed in UVB-irradiated skin. As for glycosaminoglycan (GAG) content per unit area, significant increases were observed in both Sq-OOH-treated skin and UVB-irradiated skin. Histological observation revealed epidermal hyperplasia and dermal alterations such as collagen degradation and GAG increases in Sq-OOH-treated skin. Histological changes induced by Sq-OOH were not as pronounced as those induced by UVB irradiation.

Takema et al (Takema et al, 2000) have developed a model for studying the effect of agents on age- and UV-damaged skin. UV irradiation causes similar changes in the elastic properties of skin as shown by chronically irradiating hairless mice (HR/ICR) with suberythemal doses of UVA or UVB. Skin thickness increased significantly after UVB irradiation while skin elasticity decreased significantly after UVA and UVB irradiation, and the ratio of viscosity to elasticity increased significantly after UVA irradiation. These changes are similar to those reported previously in an in vivo study on human face skin using the same instrument.

Other animal models useful for studying the effects of compounds and compositions on aging skin include transgenic mice models of cutaneous photoaging, disclosed in U.S. Pat. Nos. 5,648,061 and 6,689,936.

Example 4

Anti-Wrinkling Effects in Human Subjects

The anti-wrinkle effect obtained following application of compositions of the present invention on human subjects, is described. Female adult volunteers aged 35 to 70 were selected and the anti-wrinkle effect of different formulations are compared to that of a placebo formulation (the same formulation without the active ingredient). The formulation is applied to precisely identified sites, located at the corner of the left or right eye, according to a randomized distribution, twice a day, for 28 days. The parameter measured is cutaneous relief at the contour of the eye in lines and wrinkles referred to as crow's feet. The quantification of the different variables of the relief is carried out by methods known in the art (Sauerman et al., 2002; reviewed in Corcuff and Pierard, 1998).

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

REFERENCES

Chiba, K, Kawakami, K, Sone, T, Onoue, M. 2003. Characteristics of Skin Wrinkling and Dermal Changes Induced by Repeated Application of Squalene Monohydroperoxide to Hairless Mouse Skin. Skin Pharma. Physiol 16(4):242-251.

Corcuff P, Pierard G E. 1998. Skin imaging: state of the art at the dawn of the year 2000. Curr Probl Dermatol. 26:1-11.

Fisher G J, Kang S, Varani J, Bata-Csorgo Z, Wan Y, Datta S, Voorhees J J. 2002. Mechanisms of photoaging and chronological skin aging. Arch Dermatol 138(11):1462-70.

Fujimura T, Moriwaki S, Takema Y, Imokawa G. 2000. Epidermal change can alter mechanical properties of hairless mouse skin topically treated with 1alpha, 25-dihydroxyvitamin D(3). Dermatol Sci. 24(2):105-11.

Lehmann B, Querings K, Reichrath J. 2004. Vitamin D and skin: new aspects for dermatology. Exp Dermatol; 13 Suppl 4:11-5.

Luo Y, Toyoda M, Nakamura M, Morohashi M. 2002. Morphological analysis of skin in senescence-accelerated mouse P10. Med Electron Microsc. 35(1):31-45.

Mitani H, Naru E, Yamashita M, Arakane K, Suzuki T, Imanari T. 2004. Ergocalciferol promotes in vivo differentiation of keratinocytes and reduces photodamage caused by ultraviolet irradiation in hairless mice. Photodermatol Photoimmunol Photomed. 20(5):215-23.

Morimoto S, Yoshikawa K, Kozuka T, Kitano Y, Imanaka S, Fukuo K, Koh E, Kumahara Y. 1986. An open study of vitamin D3 treatment in psoriasis vulgaris. Br. J. Dermatol, 115(4):421-429.

Nikoloff, B J, Fisher, G J, Mitra, R S, Voorhees, J J. 1988. Additive and Synergistic Antiproliferative Effect of Cyclosporin A and Gamma Interferon on Cultured Human Keratinocytes. Amer. J. Pharmacol., 131:12-18.

Ockenfels, H M, Nußbaum, G, Schultewolter, T, Burger, P M., Goos, M. 1995. Cyclosporin A, FK506 and dithranol alter tyrosine-specific protein phosphorylation in HaCat keratinocytes. Arch. Dermatol. Res., 287:304-309.

Ohyama, Y and Yamasaki, Y. 2004. Eight Cytochrome P450s Catalyze Vitamin D Metabolism. Frontiers in Bioscience 9, 3007-3018.

Paramio, J M, and Jorcano, J L. 1997. Role of protein kinases in the in vitro differentiation of human HaCat cells. Brit. J. Dermatol, 137:44-50.

Rindelov, L L. 1983. A detergent trypsin method for the preparation of nuclei for FACS DNA analysis, Cytometry 3(5)323-327.

Sauermann K, Clemann S, Jaspers S, Gambichler T, Altmeyer P, Hoffmann K, Ennen J. 2002. Age related changes of human skin investigated with histometric measurements by confocal laser scanning microscopy in vivo. Skin Res Technol. 8(1):52-6.

Sun T-T, Green, H. 1976. Differentiation of the epidermal keratinocytes in cell culture: formation of cornified envelope, Cell 9:511-521.

Takeda T, Hosokawa M, Takeshita S, Irino M, Higuchi K, Matsushita T, Tomita Y, Yasuhira K, Hamamoto H, Shimizu K, Ishii M, Yamamuro T. 1981. A new murine model of accelerated senescence. Mech Ageing Dev. 17(2):183-94.

Takema Y, Imokawa G. 1998. The effects of UVA and UVB irradiation on the viscoelastic properties of hairless mouse skin in vivo. Dermatology 196(4):397-400.

What is claimed is:

1. A method for retarding, arresting, reversing or treating atrophy in skin of a mammalian subject in need thereof, the method comprising the step of:
    topically applying to the skin of the subject a dermatologically effective amount of a composition comprising: a first active agent of calcipotriol; a second active agent of nicotinamide; and a dermatologically acceptable carrier, thereby retarding, arresting, reversing or treating atrophy in the skin of the subject.

2. The method according to claim 1, wherein the subject is a human subject.

3. The method according to claim 1, wherein atrophy of the skin is associated with steroid-induced atrophy, menopausal induced atrophy or aging.

4. A method of treating an epidermal condition related to aging in a subject in need thereof, the method comprising the step of:
    topically administering to the skin of the subject a dermatologically effective amount of a composition comprising: a first active agent of calcipotriol; a second active agent of nicotinamide; and a dermatologically acceptable carrier, thereby treating an epidermal condition related to aging in the subject.

5. The method according to claim 4, wherein the subject is a human subject.

6. The method according to claim 4, wherein the epidermal condition related to aging is associated with chronological aging, photoaging or a combination of chronological aging and photoaging.

7. The method according to claim 4, wherein the epidermal condition is selected from at least one of the group consisting of fine lines, wrinkles, discoloration, sagging, enlarged pores, rough skin, dry skin, acne, alopecia and stretch marks.

8. The method according to claim 4, wherein the composition consists essentially of: calcipotriol; cyclic adenosine diphosphate ribose (cADPR); nicotinamide; and the dermatologically acceptable carrier, with the active agents present in amounts which, in combination, are sufficient to treat the epidermal condition related to aging in the subject.

9. A method of treating an epidermal condition related to aging in a subject in need thereof, the method comprising the step of:
    topically administering to the skin of the subject a dermatologically effective amount of a composition consisting essentially of calcipotriol; and a dermatologically acceptable carrier, thereby treating an epidermal condition related to aging in the subject.

10. The method according to claim 1, wherein the composition consists essentially of calcipotriol, nicotinamide, and the dermatologically acceptable carrier, with the active agents present in amounts which, in combination, are sufficient to retard, arrest, or reverse atrophy in the skin of the subject.

11. The method according to claim 1, wherein the composition consists of calcipotriol, nicotinamide, and the dermatologically acceptable carrier, with the active agents present in amounts which, in combination, are sufficient to retard, arrest, or reverse atrophy in the skin of the subject.

12. The method according to claim 1, wherein the composition consists essentially of calcipotriol, nicotinamide, cyclic adenosine diphosphate ribose (cADPR) and the dermatologically acceptable carrier, with the active agents present in amounts which, in combination, are sufficient to prevent, retard, arrest, or reverse atrophy in the skin of the subject.

13. The method according to claim 1, wherein the composition consists of calcipotriol, nicotinamide, cyclic adenosine diphosphate ribose (cADPR) and the dermatologically acceptable carrier, with the active agents present in amounts which, in combination, are sufficient to retard, arrest, or reverse atrophy in the skin of the subject.

14. The method according to claim 4, wherein the composition consists essentially of calcipotriol, nicotinamide and the dermatologically acceptable carrier.

15. The method according to claim 8, wherein the composition consists of calcipotriol, nicotinamide, cyclic adenosine diphosphate ribose (cADPR) and the dermatologically acceptable carrier.

* * * * *

UNITED STATES PATENT AND TRADEMARK OFFICE
CERTIFICATE OF CORRECTION

PATENT NO. : 8,034,788 B2  
APPLICATION NO. : 11/914093  
DATED : June 10, 2008  
INVENTOR(S) : Harel et al.

Page 1 of 1

It is certified that error appears in the above-identified patent and that said Letters Patent is hereby corrected as shown below:

IN THE CLAIMS:

Column 22:  
Line 25 (claim 12, line 5), delete "prevent,"

Signed and Sealed this  
Thirteenth Day of December, 2011

David J. Kappos  
*Director of the United States Patent and Trademark Office*